US011464435B2

United States Patent
Kabany

(10) Patent No.: US 11,464,435 B2
(45) Date of Patent: *Oct. 11, 2022

(54) METHOD FOR MONITORING A DRIVER OF A VEHICLE BY MEANS OF A MEASURING SYSTEM

(71) Applicant: B-Horizon GmbH, Regensburg (DE)

(72) Inventor: Mohammad Kabany, Regensburg (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/669,302

(22) Filed: Oct. 30, 2019

(65) Prior Publication Data

US 2020/0146607 A1    May 14, 2020

(30) Foreign Application Priority Data

Nov. 14, 2018  (DE) .................. 10 2018 128 550.7

(51) Int. Cl.
*B60R 22/00* (2006.01)
*A61B 5/16* (2006.01)
(Continued)

(52) U.S. Cl.
CPC ............ *A61B 5/165* (2013.01); *A61B 5/0002* (2013.01); *A61B 5/18* (2013.01); *A61B 5/486* (2013.01);
(Continued)

(58) Field of Classification Search
CPC ......... A61B 5/165; A61B 5/0002; A61B 5/18; A61B 5/486; A61B 5/6893; A61B 5/7405;
(Continued)

(56) References Cited

U.S. PATENT DOCUMENTS 6,392,550 B1* 5/2002 Najor .................. A61B 5/18
340/576
7,213,462 B2* 5/2007 Watanabe ............ G01N 27/223
73/714

(Continued)

FOREIGN PATENT DOCUMENTS

DE    10 2012 017 47 A1    3/2013
DE    10 2016 003 125 A1    10/2016
(Continued)

OTHER PUBLICATIONS

International Search Report, dated Feb. 13, 2020, for German Application PCT/EP2019/078890 filed Oct. 23, 2019.

*Primary Examiner* — Zhen Y Wu
(74) *Attorney, Agent, or Firm* — Michael J. Gallagher, Esq.; Luper Neidenthal & Logan

(57) ABSTRACT

An apparatus and method for monitoring a vehicle driver having at least one sensor for measuring pressure and/or humidity. The sensor includes at least one capacitor having at least two electrodes, which may be arranged horizontally on a flexible support material. At least one dielectric layer may be arranged between the electrodes. At least one electrode, and/or the dielectric layer, and at least one, at least partially liquid-permeable and/or liquid-absorbing moisture layer may be arranged on a side facing away from a support material. At least one electrode and/or the dielectric layer may be arranged transversely between the support material and the moisture layer. A capacitance may be changed by liquid on the dielectric layer, and a processing unit measures and/or stores values from the sensor, creating a capacitive (Continued)

humidity sensor. The processing unit may send the to a central CPU, wherein this data may be processed by the processing unit.

10 Claims, 6 Drawing Sheets

(51) Int. Cl.
*A61B 5/00* (2006.01)
*A61B 5/18* (2006.01)
*B60N 2/00* (2006.01)
*B60N 2/02* (2006.01)
*B60Q 9/00* (2006.01)
*B60W 40/08* (2012.01)
*B60W 50/14* (2020.01)
*G01L 1/14* (2006.01)
*G01N 27/22* (2006.01)

(52) U.S. Cl.
CPC .......... *A61B 5/6893* (2013.01); *A61B 5/7405* (2013.01); *A61B 5/746* (2013.01); *A61B 5/7425* (2013.01); *B60N 2/002* (2013.01); *B60N 2/0244* (2013.01); *B60Q 9/00* (2013.01); *B60W 40/08* (2013.01); *B60W 50/14* (2013.01); *G01L 1/142* (2013.01); *G01N 27/223* (2013.01); *A61B 5/4266* (2013.01); *A61B 2562/0247* (2013.01); *B60N 2002/0268* (2013.01); *B60W 2050/143* (2013.01); *B60W 2050/146* (2013.01); *B60W 2540/22* (2013.01)

(58) Field of Classification Search
CPC ..... A61B 5/7425; A61B 5/746; A61B 5/4266; A61B 2562/0247; B60N 2/002; B60N 2/0244; B60N 2002/0268; B60Q 9/00; B60W 40/08; B60W 50/14; B60W 2050/143; B60W 2050/146; B60W 2540/22; G01L 1/142; G01N 27/223
USPC .............................................. 340/49; 701/49
See application file for complete search history.

(56) References Cited

U.S. PATENT DOCUMENTS

| | | | | |
|---|---|---|---|---|
| 2003/0096593 | A1* | 5/2003 | Naboulsi | G08B 21/06 455/565 |
| 2004/0209594 | A1* | 10/2004 | Naboulsi | H04M 1/6083 455/403 |
| 2006/0037404 | A1* | 2/2006 | Watanabe | G01N 27/223 73/714 |
| 2012/0000285 | A1* | 1/2012 | Waga | G01N 27/225 29/595 |
| 2012/0101690 | A1* | 4/2012 | Srinivasan | A61B 5/6887 600/509 |
| 2013/0139587 | A1* | 6/2013 | Le Neel | G01N 27/223 216/13 |
| 2013/0194099 | A1* | 8/2013 | Nagata | B60K 28/06 340/575 |
| 2013/0325202 | A1* | 12/2013 | Howard | B60W 30/08 701/1 |
| 2014/0026678 | A1* | 1/2014 | Cannard | D04B 21/14 73/862.391 |
| 2014/0125359 | A1* | 5/2014 | El-Gamal | G01L 9/12 324/664 |
| 2014/0139241 | A1* | 5/2014 | Sakai | G01N 27/223 324/665 |
| 2015/0277579 | A1* | 10/2015 | Naboulsi | H04M 1/6083 345/156 |
| 2016/0202201 | A1* | 7/2016 | Cobianu | G01N 27/414 73/335.04 |
| 2017/0082567 | A1* | 3/2017 | O'Brien | G01N 27/223 |
| 2017/0101111 | A1* | 4/2017 | Fung | B60K 35/00 |
| 2017/0138881 | A1* | 5/2017 | Krapf | G01N 33/383 |
| 2018/0165568 | A1* | 6/2018 | Khoche | G06K 19/07773 |
| 2019/0011288 | A1* | 1/2019 | Nassar | G01D 21/00 |

FOREIGN PATENT DOCUMENTS

DE     10 2017 111 908 A1     11/2017
DE     10 2018 128 550.7     8/2019

* cited by examiner

METHOD FOR MONITORING A DRIVER OF A VEHICLE BY MEANS OF A MEASURING SYSTEM

DESCRIPTION

The present invention relates to a method for monitoring a driver of a vehicle by means of a measurement system and to a corresponding apparatus according to claims 1 and 9.

The method proposed here inter alia comprises the first step in which at least one measurement system for measuring pressure and/or humidity is provided, wherein the measurement system is coupled to at least one vehicle element or is installed with at least one in an integrated manner. In this case, the measurement system has at least one sensor for measuring a stress level, preferably only one stress level of the driver such that the sensor measures pressure and/or humidity.

In a second step, the measured stress level values, i.e. the pressure and/or humidity values, are subsequently forwarded to a processing unit of the measurement system.

In a third step, a stress level of the driver is detected and recognised based on the stress level values.

In a fourth step, a selected action is selected based on the recognition by the measurement system, wherein the action is selected from a list consisting of: setting up a call to a remote support centre, transmitting the stress level values to a remote support centre, generating an audible alarm and generating a visual alarm, adjusting a volume of speakers in the vehicle, adjusting a seat position of a vehicle seat of the vehicle, and displaying break recommendations to the driver.

However, music adjustment also comes into question as a possible action. This may mean that the music channel is changed. For this purpose, it is conceivable that the music channel on a vehicle radio is automatically changed to a music app. For this purpose, it is conceivable that this music app is stored in advance in the processing unit or in another unit and for this music app to be loaded fully automatically if at least one stress level value is exceeded. This music app can then fully automatically play at least one previously stored music track, in particular to calm the driver down such that the stress level values decrease. Alternatively or in addition to this, internal vehicle lighting can also be adjusted. An appropriate setting can be referred to as 'ambient light' such that a light colour, a light intensity and a brightness are set.

In particular, a pressure measurement and/or humidity measurement in connection with a stress level, inter alia, is/are claimed in the present invention. The humidity measurement is based in particular on the release of sweat on the skin of the driver, which touches a usage object in the vehicle (steering wheel, joystick, radio, etc.) from the outside and by means of the skin.

A stress level is defined as the stress (impact of loads) on a person due to internal and external stimuli or loads (objective factors affecting people as well as the magnitudes and time periods thereof). Said loads can be both artificial and natural, be both biotic and abiotic, act on the body as well as on the human psyche and ultimately be perceived as positive or negative or have an impact. Managing stress is dependent on the personal (and health) characteristics and cognitive abilities of the individual, and dealing with a threat is also referred to as coping. Usable behaviours are, for example, aggression, flight, behavioural alternatives, acceptance, a change of condition or denial of the situation.

Stressors that put the organism under stress but have a positive effect are referred to as positive stress or eustress (the Greek prefix εὖ (eu) means 'well, good, true'). Positive stress improves attention and promotes maximum performance of the body without harming it. Eustress occurs, for example, when a person is motivated to perform and then has the time and opportunities to prepare for this, or if a (possibly long-term or severe) crisis situation or disease can still be addressed, managed (coping strategy) and overcome in a positive manner. As a result, moments of happiness can even be experienced. Eustress also has a positive effect on the mental or physical functioning of an organism, even if it occurs frequently and over a longer period of time.

Stress is only perceived negatively if it occurs frequently or permanently and cannot be compensated for physically and/or mentally and is therefore considered unpleasant, threatening or overstraining. In particular, negative effects can occur if the individual sees or has no way of overcoming the situation, which can also be due to their interpretation of the stimuli. Examples of this are exams without the time or capacity to study, a disease that is unknown or unrecognised despite a visit to a doctor (cf. Semmelweis reflex), a flat made unbearable by noise without the possibility of moving or the like. In this case, persistent negative stress (also referred to as distress or dystress; the Greek prefix δύς (dys) means 'ill, bad') can be prevented by means of suitable aids or stress management strategies.

Abiotic stress factors would be, for example, of a physical nature, such as cold, heat, noise, exhaust gases and natural and artificial radiation. The latter include, for example, strong and excessively prolonged solar radiation or other, such as high-frequency or radioactive or electromagnetic radiation. Furthermore, toxic substances, for example plasticisers such as diethylhexyl phthalate (DEHP) in PVC floor coverings or children's toys, (cigarette) smoke and the substances contained therein, drinking water pollution, excessive and regular alcohol consumption, a diet low in nutrients or pesticides increasingly used in a variety of agricultural products and methods of application (for example 'weed control' using glyphosate) and thereby absorbed into the human body.

Biotic factors include, for example, stress caused by pathogens or tumours, as well as chronic and autoimmune inflammatory processes, which, however, are in turn influenced by the above-mentioned abiotic factors (stressors having an impact on cell metabolism and the immune system). On an emotional level, mental stresses such as bullying, certain attitudes and expectations of a person or, for example, of their parents, and fears can also be stressors (psychosocial stress factors).

Stress is therefore first the strain on the body caused by such stressors. This is followed by a reaction and possibly an adaptation of the body to these factors, if necessary with external aid. Distress leads to a greatly increased tension in the body (release of certain neurotransmitters and hormones, for example epinephrine and norepinephrine) and, in the long term, to a decrease in attention and performance. Stress or distress only has a harmful effect on the human body if stress takes place beyond the range of adaptation and repair functions (for example DNA repair) of the individual or of their body that are possible according to their individual physique and psyche or health condition (chronic stress/duration of exposure, excess, possibly multiple factors).

According to at least one embodiment, only the pressure and the humidity are measured by the sensor to determine a stress level of the driver.

According to at least one embodiment, the sensor is installed in a steering wheel and/or a joystick and/or a vehicle seat of a vehicle such that the driver directly touches the steering wheel and/or the joystick and/or the vehicle seat.

According to at least one embodiment, a memory of the CPU stores limit values of pressure and/or humidity, wherein the pressure and temperature values measured in a time-discrete or continuous manner in each case are compared to the values stored in the memory of the CPU, wherein the CPU determines an action to execute (for example one of the above actions) if at least one of these values (humidity and pressure) is exceeded.

According to at least one embodiment, a memory of the CPU stores factor limit values of pressure and humidity, wherein the pressure and temperature values measured in a time-discrete and continuous manner in each case are compared to the values stored in the memory of the CPU, wherein the CPU determines an action to execute (for example one of the above actions) if at least one of these values (humidity and pressure) is exceeded, wherein the factor limit value is defined as a factor of the respective pressure and humidity value, in particular wherein the sensor measures both values at the same time.

According to at least one embodiment, the pressure and the humidity are in each case measured at different times within a predetermined measurement time interval. Experience has shown that the pressure increases first during a stress reaction, and only after that does perspiration begin to form with a time delay. Simply put, the driver initially grips, for example, a steering wheel particularly strongly in the event of a stress situation, the corresponding formation of perspiration only occurring afterwards. Value pairs can be formed from the pressure values and the associated humidity values.

According to at least one embodiment, the pressure and/or the temperature is/are measured first and the humidity and/or the temperature is/are only measured afterwards within the measurement time interval, wherein the pressure and the humidity are measured only once within each measurement time interval.

According to at least one embodiment, a time interval between two measurement intervals immediately adjacent to each other in terms of time is greater than the period of at least one of the measurement intervals, in particular wherein no measurement takes place in measurement breaks generated thereby. Such a measurement can be carried out in time cycles and in a non-time-continuous manner.

Furthermore, the present application relates to an apparatus for monitoring a driver of a vehicle by means of a measurement system for carrying out the method.

According to at least one embodiment, the apparatus comprises at least one measurement system for measuring pressure and/or humidity, wherein the measurement system is coupled to at least one vehicle element or is installed or installable with at least one in an integrated manner, wherein the measurement system has at least one sensor for measuring a stress level, preferably only one stress level of the driver such that the sensor can measure pressure and/or humidity.

The present invention further relates to a measurement system for measuring pressure and/or humidity and to a method for measuring pressure and/or humidity. The measurement system described here can be one that is used in the above-described method for monitoring a driver of a vehicle by means of a measurement system and the corresponding apparatus.

The measurement system according to the invention for measuring pressure and/or humidity comprises at least one sensor for measuring pressure and/or humidity, wherein the sensor comprises at least one capacitor having at least two electrodes, which are arranged relative to each other, in particular in a horizontal direction, along and on an, in particular flexible, support material, wherein at least one dielectric layer is arranged between the electrodes.

The horizontal direction is preferably a main extension direction of the flexible support material.

In this context, 'flexible' means that the support material is bendable and thus resilient at least in some places.

In particular, the support material may be a woven fabric or another clothing fabric such as, for example, a polyester.

The dielectric layer thus spaces the two electrodes in a horizontal and/or in a transverse direction perpendicular thereto.

According to the invention, at least one electrode and/or the dielectric layer, at least in some places, and at least one, at least partially liquid-permeable and/or liquid-absorbing moisture layer is/are arranged on a side facing away from the support material, wherein the at least one electrode and/or dielectric layer is/are thus arranged in a transverse direction between the support material and the moisture layer such that a capacitance is at least partially changed by the liquid at least partially incident on the dielectric layer, wherein a processing unit is configured and provided for measuring and/or storing the measured values of the sensor such that a capacitive humidity sensor is produced.

A capacitive humidity sensor is in principle a capacitor of which the dielectric preferably consists of a hygroscopic polymer layer which takes up (absorbs) or releases (desorbs) moisture according to the humidity of the ambient air until an equilibrium state (diffusion gradient=0) is reached. The dielectric constant of the polymer material changes as a function of a moisture content.

The object of the processing unit is, inter alia, to determine the relative humidity as accurately as possible from a measured ambient temperature and the moisture-dependent capacitance value of the sensor.

According to the invention, the processing unit sends the data measured by the sensor to a central processing unit (CPU), wherein this data is processed by the processing unit. The CPU and the processing unit are preferably different from each other. For example, the CPU and the processing unit are spaced apart from each other. In particular, the processing unit and the CPU cannot be arranged on a common support and/or substrate unless the support is the support material, that is, for example, a textile.

It is also conceivable for the apparatus claimed here, and in particular the sensors, to be installed on an inner surface of a tyre. It is also conceivable for the sensors to even be inserted into the material of the tyre. It is conceivable for all the sensors to be inserted into the material and thus encased by the material of the tyre and for the processing units to be arranged on the inner surface of the tyre. Alternatively, however, the processing units can also be incorporated into the material of the tyre. The sensors can then detect the internal tyre pressure, the internal tyre temperature and/or the individual or total running time of the tyre.

According to at least one embodiment, the measurement system comprises at least one apparatus for measuring pressure and/or humidity, wherein the apparatus has at least one sensor for measuring pressure and/or humidity, wherein the sensor comprises at least one capacitor having at least two electrodes, which, in particular in a horizontal direction, are arranged relative to each other along and on an, in particular flexible, support material, wherein at least one dielectric layer is arranged between the electrodes.

According to the invention, at least one electrode and/or dielectric layer, at least in some places, and at least one, at least partially liquid-permeable and/or liquid-absorbing layer (=moisture layer) is/are arranged on a side facing away from the support material, wherein the at least one electrode and/or dielectric layer is/are thus arranged in a transverse direction between the support material and the moisture layer such that a capacitance is at least partially changed by the liquid at least partially incident on the dielectric layer, wherein a processing unit is configured and provided to measure and/or store these measured values of the sensor such that a capacitive humidity sensor is created.

According to the invention, the processing unit sends the data measured by the sensor to a central processing unit (CPU), wherein this data is processed by the processing unit.

The sensor and/or the processing unit and/or the CPU can be supplied with electrical energy by means of a battery or a fixed mains power supply.

Alternatively or additionally, the generation of electrical energy for supplying the sensor and/or processing unit by means of so-called "energy harvesting" is possible.

Energy harvesting refers to the recovery of small quantities of electrical energy from sources such as ambient temperature, vibrations or air flows for mobile apparatuses with low power. The structures used for this purpose are also called nanogenerators. In wireless technologies, energy harvesting avoids limitations by wired power supply or batteries.

Possibilities of energy harvesting:
Piezoelectric crystals generate electrical voltages when force is exerted, for example by pressure or vibration. These crystals can be arranged at or on the support material.
Thermoelectric generators and pyroelectric crystals gain electrical energy from temperature differences. These generators can be arranged at or on the support material.
The energy of radio waves, a form of electromagnetic radiation, can be captured and used energetically via antennas. An example of this is the passive RFIDs. These antennas may be arranged at or on the support material.
Photovoltaics, electrical energy from the ambient light.
Osmosis.

An energy accumulator of the apparatus can be part of a processing unit. For this purpose, one or a plurality of the processing units can have such an energy accumulator (local energy accumulators). For example, only one or some of the processing units has such an energy accumulator such that one of these processing units supplies electrical energy to another processing unit (namely one that has no energy accumulator).

It is also conceivable for the energy storage unit(s) of the processing unit(s) to supply the CPU with electrical energy wholly or in part. For example, the CPU can thus be connected to no other energy accumulators and/or power supply lines.

At least one of the energy accumulators can be charged via the energy harvesting mentioned above.

The energy transmission between the sensors and/or the processing units and/or the CPU can be wholly or in part wireless.

For example, the wireless energy transmission in the near field, also referred to as non-radiative coupling, includes inductive coupling, which is based on magnetic flux. The term 'wireless energy transmission' is frequently used synonymously for inductive energy transmission because it plays a dominant role in practical applications. Wave phenomena play no role in non-radiative coupling in the near field.

For example, the wireless energy transmission between the individual elements occurs by means of inductive coupling, resonant inductive coupling and/or capacitive coupling.

According to at least one embodiment, the measurement system has at least two sensors, wherein the processing unit divides the sensors into groups of at least one sensor on the basis of at least one of the following criteria:
location of the sensor or the sensors on the support material, wherein the support material is divided into surface regions and only sensors of one group are arranged within a surface region,
surface area of a sensor.

According to at least one embodiment, the measurement system comprises at least two apparatuses for measuring pressure and/or humidity, wherein each processing unit forwards the data received from the sensors to the CPU. The data connection between the processing unit and the CPU can be wired (with data connections) or wireless. For this purpose, at least one processing unit can establish a Bluetooth connection to the CPU.

According to at least one embodiment, at least one apparatus comprises at least two sensors. In this respect, a sensor group can already be formed by these two sensors. The two sensors can then be controlled and/or regulated by a common processing unit.

It is conceivable for the plurality of processing units to form a processing network, wherein the collection, processing and/or transmission of the sensor data and/or of the processing data of each sensor and/or of each processing unit is/are controlled by at least one control device (master). The control unit can be identical to the CPU described above.

However, it is also possible for one or a plurality of the processing units to constitute the master, which controls the remaining processing units (slave) and/or the other sensors (slave).

For example, one of the processing units and/or the CPU can, after the apparatus is put into operation (for example after the apparatus is switched on), select the sensors which are put into operation for a predeterminable period of use. Alternatively, all or some sensors can be put into operation; however, it is then conceivable for a processing unit and/or the CPU, in particular for the purpose of saving energy, to forward only data from a predetermined number of sensors (i.e. less than all the sensors) to the CPU (filtering).

This master processing unit can preferably communicate with the CPU as a single unit. Further alternatively or additionally, it is conceivable for one or all the processing units and/or a sensor (slave or master) to communicate directly with the CPU.

According to at least one embodiment, the processing network can be subdivided into at least two network segments (VLANs), which are only logically separated from each other, by means of at least one VLAN switch, wherein each of the detection elements is controllable as a function of controlling by means of a VLAN switch and/or of the control device and thus by means of each of the network segments.

If, for example, a very large area (for example a textile) is equipped with a plurality of sensors and processing units claimed here, individual processing units and/or sensors can then be categorised in a particularly simple manner (according to different priorities, etc.). Thus, in one embodiment, a 'virtual', i.e. VLAN subdivision is selected instead of a physical network subdivision. This ensures that it is possible to react to changes in the categorisation of the processing units and/or sensors particularly quickly and without laborious conversion work.

According to at least one embodiment, the measurement system comprises at least one processing network, wherein the processing network is subdivided into at least two network segments (VLAN), which are only logically separated from each other, by means of at least one VLAN switch of said processing network, and wherein each of the processing units and/or each of the sensors is/are controllable as a function of the controlling by means of the VLAN switch and by means of each of the network segments.

For this purpose, the VLAN switch can be installed in at least one of the processing units and/or sensors or in a separate component.

According to at least one embodiment, a prioritisation of the individual network segments is carried out by means of the VLAN switch, in particular with regard to the data exchange thereof.

According to at least one embodiment, each processing unit and/or each network segment is/are assigned at least one VLAN ID, wherein at least one sensor or one other processing unit can be controlled via each of the VLAN IDs. Individual sensors and/or individual processing units can form their own subnetwork.

Static project-dynamic routes are used in the prior art to communicate across network boundaries. This model of separation is clear and concise and has been used for years. However, this has the disadvantage that broadcast requests in the subnet are visible to all subscribers and would have to be viewed from the endpoints. In other words, it has so far been possible to control different mobile terminals only via corresponding separate and physically isolated switches which are assigned to each subnet. However, such a construction is particularly expensive and large in design.

As already mentioned above, the configuration of each subnetwork with a separate switch and separate physical data lines is thus dispensed with such that a single physical structure can be used for the entire network, wherein this physical structure, i.e. network architecture, is separated only on the basis of a logical, in particular mathematical distinction (i.e. imagined to be separated).

In this case, the abbreviation 'VLAN switch' refers to a network switch which is set up and intended to also operate a network in the form of a virtual local area network (VLAN).

In this respect, the network segments now claimed, which can each be designed in the form of a VLAN network, thus allow the network to be separated into a plurality of logical segments, i.e. into the network segments.

Unlike the physical separation by means of the assignment to a switch port, the devices are logically separated by a VLAN ID when disconnected by VLANs. In this case, the data stream of each station is provided with an identifier (the VLAN 'tag'). This identifier determines the affiliation of a data packet with a specific VLAN. All the devices having the same VLAN ID are now in a logical network.

In particular, a broadcast can be limited by the logical separation of the individual networks. Broadcasts are distributed only to members of the same VLAN and not to all the control elements attached to the switch.

In this respect, this also contributes not only to higher performance, but also to greater security, because the data traffic is limited to fewer addressees. In addition, users or the control elements on a VLAN usually have no way to break out of the assigned VLAN. Access to (or an attack against) another computer that does not belong to its own VLAN can therefore already be prevented by the network switch. If cross-VLAN communication is necessary, routes can be explicitly set up for this purpose.

In particular, it is pointed out that the VLAN technology described herein can be one that is adapted to and/or compatible with the IEEE 802.1Q industry standard.

The IEEE 802.1Q standard is a prioritisation and VLAN technology standardised by the IEEE that implements packet-based tagged VLANs, unlike the older, port-only VLANs. The term 'tagged' derives from the term 'material tags'.

Therefore, tagged VLANs are networks that use network packets that have a specific VLAN tag.

In particular, data fields for VLAN tagging are defined in the 802.1Q standard, which data fields can be introduced in the data area of an Ethernet packet.

In this respect, the present network can be designed in the form of an Ethernet communications system.

This has the advantage that existing, older switches can usually also forward such packets. The inserted tag usually consists of a plurality of fields, for example four fields of an overall length of 32 bits.

Two bytes are used for the protocol ID, 3 bits are used for the priority field, 1 bit is used for the indicator of the canonical format and 12 bits are used for the VLAN ID.

To uniquely identify a VLAN, each VLAN is therefore first assigned a unique number. This number is called a VLAN ID. A detection module equipped with the VLAN ID=1 can communicate with any other device on the same VLAN, but not with a device on another VLAN, such as ID=2, 3, etc.

In order to differentiate between the VLANs, an Ethernet frame is extended by 4 bytes according to the IEEE 802.1Q standard. Of these, 12 bits are provided to accommodate the VLAN ID such that, in theory, 4096−2=4094 VLANs are possible (without using the canonical format).

It is conceivable for the individual logical network connections to be designed according to an OPC standard, i.e. for example, in the form of OPC UA connections. In particular, it is conceivable for a plurality of OPC UA endpoints having different IP addresses, VLAN IDs and prioritisations according to the above IEEE 802.1Q standard to be available for each network segment via the control device.

If a network segment, which has been allocated a specific VLAN ID in an unambiguous, preferably one-to-one manner, has higher priority than a network segment of a correspondingly different VLAN ID, which differs only logically therefrom, then the control device and/or the VLAN switch can be provided to initially to prefer the data exchange of the higher-priority network segment in order to allow processing of the lower-priority network segment only after the tasks assigned to this higher-priority network segment have been cleared.

In other words, the following generally applies: Assignment and configuration of the OPC UA endpoints to a specific network segment according to the VLAN ID and assignment of a priority according to the priority of the corresponding VLAN.

According to at least one embodiment, at least one VLAN ID is assigned to each sensor and/or processing unit and at least one, for example exactly one VLAN ID is assigned to each network segment in an unambiguous, preferably oneto-one manner, wherein at least one control element can be controlled via each of the VLAN IDs. According to at least one embodiment, at least one apparatus comprises at least one temperature sensor, wherein the temperature sensor measures an ambient temperature and/or a temperature of a sensor and forwards it to the processing unit of an apparatus and/or to the CPU.

According to at least one embodiment, the CPU determines a degree of utilisation (CPU load and/or memory consumption) of at least one processing unit, wherein the power of the sensor(s) is at least in part throttled or switched off completely if a limit temperature of the processing unit and/or at least of the sensor assigned to said processing unit is exceeded.

In addition, according to at least one embodiment, the sensor is a capacitive pressure sensor, wherein the processing unit is additionally configured and provided for measuring and/or storing a capacitance change of the capacitor caused by external pressure.

In principle, a capacitive sensor is therefore a sensor which operates on the basis of the change in the electrical capacitance of a single capacitor or of a capacitor system. The influencing of the capacitance by the value to be detected can be done in various ways, which are primarily determined by the intended use.

Among other things, a capacitive sensor is based on two electrodes, one of which can be the surface to be measured, forming the "plates" of an electrical capacitor of which the capacitance or capacitance change is measured, which can be influenced as follows:

A plate is displaced and/or deformed by the effect to be measured, thereby changing the plate spacing and thus the electrical measurable capacitance.

The plates are rigid and the capacitance itself changes by bringing an electrically conductive material or a dielectric into immediate proximity.

The effective plate area changes by sliding the plates against each other as in a rotary capacitor.

In order to be able to better detect even small changes, the actual measuring electrode can often be surrounded by a shielding electrode which shields the inhomogeneous edge region of the electric field from the measuring electrode, thereby resulting in an approximately parallel electric field between the measuring electrodes of the usually earthed counterelectrode and the known characteristic of an ideal plate capacitor.

A capacitive pressure sensor is in particular one in which the capacitance change due to the flexing of a membrane and the resulting change in the plate spacing is evaluated as a sensor effect. For example, the membrane is the above-mentioned dielectric or else the individual capacitor electrodes, which may be designed in particular in the form of a plate. In other words, in such an embodiment a capacitive humidity sensor is combined with a capacitive pressure sensor in a novel way, but without these components forming separate elements or two separate sensors, but in the present embodiment it is a "two in one" concept in which the same sensor functions both as a moisture sensor and also as a pressure sensor.

In accordance with at least one embodiment, the support material is a woven fabric, in particular into which electrical conductor paths for electrical contacting of the sensor and the processing unit are woven.

In the context of the invention, a woven fabric is therefore a fabric which has been woven manually or mechanically on the basis of individual threads.

The electrical conductor paths can therefore additionally be integrated in a fabric in addition to the usual fibres and fabric strands or replace individual fabric strands which form the fabric mesh.

Depending on the spacing and properties of the individual threads (twisted, bulked, etc.), quite loose fabrics such as bandage fabrics, or dense fabrics such as brocade material can be produced. For lengthwise resilience, fabrics are used in which rubber threads (more tapes used) or crinkled and bulked yarns are used as warp threads. They are stretched, processed and contract in the resting state. Bulked yarns consist of textured, i.e. crinkled synthetic fibres. The crinkling changes the properties of the synthetic fibres. The spun yarns are very resilient and voluminous and have a good thermal insulation.

For example, the support material may be part of an upholstery material of a seat, in particular a vehicle seat or an office chair. In this respect, the sensor, but preferably the entire apparatus, can be applied to the upholstery material of such a seat or can be integrated into such a material.

For example, the processing unit is configured and provided for detecting the individual humidity and pressure values and for determining from a combination of the individual moisture and pressure values at least one respective characteristic value from which it can be deduced which individual (with weight and/or size) just occupied the vehicle seat.

For example, from the pressure measurement by the processing unit, a weight of the respective person can be deduced and determined. Also, the respective moisture which the respective person delivers to the sensor can be measured, wherein the respective characteristic value is, for example, a product of the relative humidity value times the load weight determined by the processing unit.

If such a characteristic value exceeds a corresponding limit value, the processing unit can issue a warning, in particular by means of a connection to the electronics of the vehicle. This warning may mean that the seat is overloaded or the driver is sweating too much. However, this warning can also be replaced by an appropriate indication as to which type of occupancy is using the seat. An occupancy type can be a weight classification of a respective user, or else it can be a question of whether the user is an animal, a person or even an object. Preferably, therefore, the processing unit can be integrated into a display electronics of the vehicle but at least connectable thereto.

For this purpose, it is conceivable that the processing unit connects to a receiving unit of the vehicle, for example by means of Bluetooth or another wireless connection, and the respective identification or limit value and/or the respective warning and/or the respective identification of the user are reproduced on a display of the vehicle.

Alternatively or additionally, it is conceivable that these individual values and/or identifications can also be retrieved externally and/or displayed externally. For example, the car may be monitored for overloading by an external controller.

For example, by means of a data link, the processing unit may be in communication with an activation unit of an airbag so that the processing unit can also control and/or regulate the activation unit, in particular with regard to an activation time of the airbag. Additionally and/or alternatively, it is possible for the processing unit to supply a controller unit of the airbag with data, for example, regarding the occupancy type, position and/or weight of a user of the vehicle seat.

These data may result in the activation time and activation sequence of the airbag being adapted to the user, thereby avoiding personal injury to the user.

According to at least one embodiment, at least one electrode and/or dielectric layer is printed on the support material or on a layer, in particular a water-impermeable layer, arranged on the support material or is applied by means of a thin-film method.

This means that at least one element, preferably both the electrode and the dielectric layer, are printed on the support material or on a layer applied between the sensor and the support material, preferably an electrically non-conductive, more preferably water-impermeable layer, by means of a printing process.

The printing process may be, for example, an inkjet process.

For example, the processing unit is applied to the support material in the same manner as the sensor. For this purpose, it is conceivable that the processing unit, but at least one, in particular conductive, layer of the processing unit is printed on the support material, for example. The data communication between the processing unit and the sensor can then be produced over the above-mentioned conductor paths. These conductor paths can be woven at least partially, but preferably completely, into the woven fabric or even form individual fibres of the woven fabric itself.

For example, at least one electrode is made flat. That means that a thickness of the electrode is negligible compared to its surface area. Such an electrode can therefore be produced in particular by means of a printing process.

Alternatively, a thickness of at least one electrode may be at most 5 mm. For this purpose, the printing method can be applied several times, so that at least two, but preferably more, individual printing layers are stacked on top of each other.

Furthermore, the electrode can also be arranged on the support material by means of a 3D printing method.

1. FDM Method (Fused Deposition Modelling)

Alternative names: Fused filament fabrication (FFF), fused layer modelling (FLM) The method refers to applying (extruding) a material in layers by means of a hot nozzle. The consumable material is located, in the form of a long wire (so-called filament), on a roller and is moved by the conveying unit into a print head, melted there and applied to a printing bed. The print head and/or printing bed are movable in three directions in this case. Plastics layers can thus be gradually applied to one another.

2. The SLS Method (Selective Laser Sintering)

In contrast to the sintering method, in which materials in powder form are bonded to one another under the action of heat, in the SLS method this takes place selectively by means of a laser (alternatively also an electron beam or an infrared beam). Therefore, only a specific part of the powder is melted together.

For this purpose, a thin powder layer is always applied to the printing bed by the coating unit. The laser (or another energy source) is then directed precisely to individual points of the powder layer in order to form the first layer of the print data. In this case, the powder is melted or fused and is then solidified again by slight cooling. The unmelted powder remains around the sintered regions and is used as supporting material. After a layer is solidified, the printing bed is lowered by a fraction of a millimetre. The coating unit moves over the printing bed and applies the next powder layer. Subsequently, the second layer of the print data is sintered by the laser (or another energy source). This produces a three-dimensional object in layers.

3. Three-Dimensional Printing (3DP)

The 3DP method functions very similarly to selective laser sintering, but instead of a directed energy source, a print head travels over the powder. Said print head deposits tiny droplets of a binding agent onto the underlying powder layers, which are thus bonded to one another. Otherwise, this method is identical to the SLS method.

4. Stereolithography (SLA)

Instead of a plastics wire or printing material in powder form, liquid resins, known as photopolymers, are used in the stereolithography method. Said resins are hardened in layers by UV radiation and therefore produce three-dimensional objects. For this purpose, the build platform is gradually lowered in the resin tank. There are also variants (so-called polyjet methods) without an entire tank of liquid resin. For this purpose, an epoxy resin is applied in droplets out of a nozzle and is immediately cured by a UV laser.

5. Laminated Object Manufacturing (LOM)

Alternative name: Layer laminated manufacturing (LLM)

The method is based neither on chemical reactions nor on a thermal process. Here, a film or plate (e.g. paper) is cut along the contour by means of a separating tool (e.g. a knife or carbon dioxide laser) and the parts are bonded together in layers. The lowering of the build platform therefore produces a layered object made of bonded films lying one on top of the other.

One or more water-impermeable layers and/or also the moisture layer can be applied in the same manner and/or thickness as the electrode.

According to at least one embodiment, the moisture layer completely covers the capacitor. This may mean that the moisture layer delimits and closes off the sensor to the outside, i.e. in the transverse direction, so that the sensor is arranged between the moisture layer and the support material.

According to at least one embodiment, the sensor has at least one further capacitor, which is arranged in the transverse direction below or above the capacitor and is arranged on or below a further water-impermeable layer and is spaced apart from the capacitor by this water-impermeable layer, so that a capacitor stack is formed.

The further capacitor may be constructed in the same way as the capacitor and may also be arranged in the same way as the capacitor on the further water-impermeable layer.

By means of such a capacitor stack, the sensor technology can be refined in a particularly simple manner, namely insofar as it is conceivable that, in the case of two sensors forming the capacitor stack, both sensors perform the same tasks, but respective measured values which, taken together, allow a mean value to be inferred are determined by the individual sensors. For example, the (relative) humidity of the environment is measured by each of the two sensors, wherein the moisture mean value is then determined from these two measured values. The same can apply correspondingly to the pressure measurement, so that the accuracy of the entire measurement, in particular a combination of the measurements of (relative) humidity and the respective pressure can be made very accurate.

According to at least one embodiment, the water-impermeable layer and/or the further water-impermeable layer at least partially form(s) the dielectric layer itself.

This may mean that instead of the separate positioning of a dielectric layer next to the water-impermeable layer and/or next to the further water-impermeable layer, this dielectric layer itself is formed by the water-impermeable layer and/or the further water-impermeable layer.

Such a production of the dielectric layer by the water-impermeable layer(s) therefore forms a particularly simple and cost-effective production method for a cost-effective apparatus.

Apart from that, it can basically be provided that the electrodes, the dielectric layer and the water-impermeable layer(s) are arranged in such a way that an electrical short-circuit is prevented in any case.

According to at least one embodiment, a maximum thickness of the moisture layer is at least 30% and at most 80% of the maximum thickness of the water-impermeable layer and/or the maximum thickness of the further water-impermeable layer.

This not only ensures a particularly flat sensor, but also it ensures a particularly fast response time to humidity changes. The humidity acting from outside on the moisture layer therefore does not have to travel long distances to the dielectric.

Furthermore, the present invention relates to a method for measuring pressure and/or humidity, wherein, in particular, it should be noted that all the features disclosed for the apparatus described above are also disclosed for the method described here, and vice versa.

According to at least one embodiment, the method for measuring pressure and/or moisture initially comprises a first step by means of which at least one measurement system, in particular according to at least one of the preceding claims, is provided, wherein the measurement system provides at least one sensor for measuring pressure and/or humidity, wherein the sensor has at least one capacitor having at least two electrodes, which are arranged relative to each other, in particular in a horizontal direction along and on an, in particular flexible, support material, wherein at least one dielectric layer is arranged between the electrodes.

According to the invention, at least one electrode and/or the dielectric layer, at least in some places, and at least one, at least partially liquid-permeable and/or liquid-absorbing moisture layer is arranged on a side facing away from the support material, wherein the at least one electrode and/or the dielectric layer is/are thus arranged in a transverse direction between the support material and the moisture layer such that a capacitance is at least partially changed by the liquid at least partially incident on the dielectric layer, wherein a processing unit measures and/or stores this change such that a capacitive humidity sensor is produced.

In this case, the method described above has the same advantages and advantageous embodiments as the apparatus described above. dr In the following, the invention described here will be described in greater detail with reference to two embodiments and the associated drawings.

Like or analogous components are provided with the same reference signs.

FIG. 1A shows a method 200 and an apparatus 100 for monitoring a driver of a vehicle by means of a measurement system 1000.

In this case, the method 200 comprises a first step according to which a measurement system 1000 for measuring pressure and/or humidity is provided, wherein the measurement system 1000 is coupled to at least one vehicle element 100A or is installed with at least one in an integrated manner, and the measuring system 1000 has at least one sensor 1 for measuring a stress level, preferably only one stress level of the driver such that the sensor 1 measures pressure and/or humidity.

Subsequently, the measured stress level values, i.e. the pressure and/or humidity values, are forwarded to a processing unit 5 of the measurement system 1000, wherein the stress level of the driver is recognised on the basis of the stress level values in a further step.

In a further step, an action is selected based on the recognition by the measurement system 1000, wherein the action is selected from a list consisting of: setting up a call to a remote support centre, transmitting the stress level values to a remote support centre, generating an audible alarm and generating a visual alarm, adjusting a volume of speakers in the vehicle, adjusting a seat position of a vehicle seat of the vehicle, and displaying break recommendations to the driver.

Figure 2A:
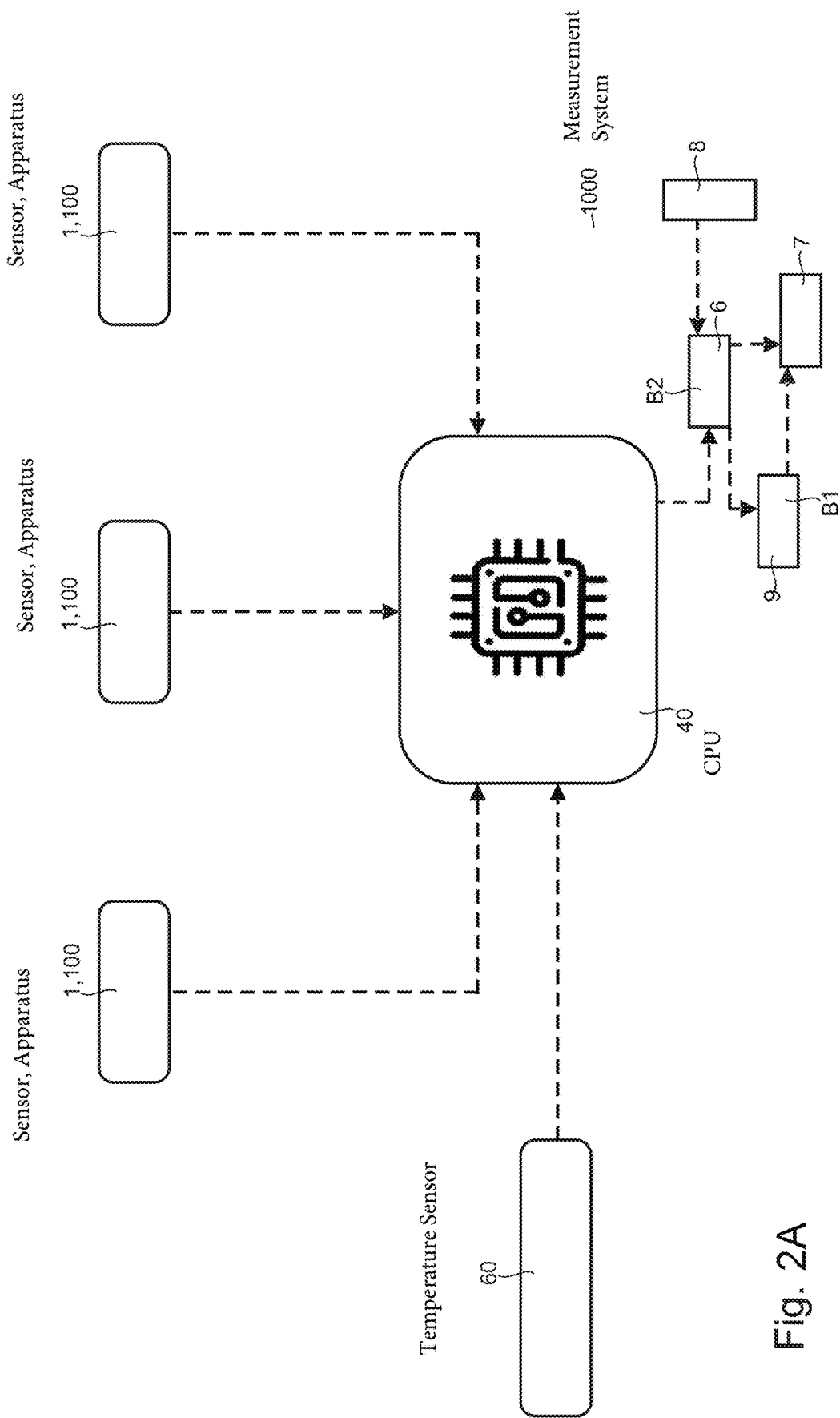
FIG. 2A to 2C show an embodiment of a measurement system described here and according to the invention.

In this case, a memory of a CPU 40, which can be seen in FIG. 2A, stores limit values of pressure and/or humidity, wherein the pressure and temperature values measured in a time-discrete or continuous manner in each case are compared to the values stored in the memory of the CPU 40, wherein the CPU 40 determines an action to execute if at least one of these values (humidity and pressure) is exceeded.

Figure 1A:
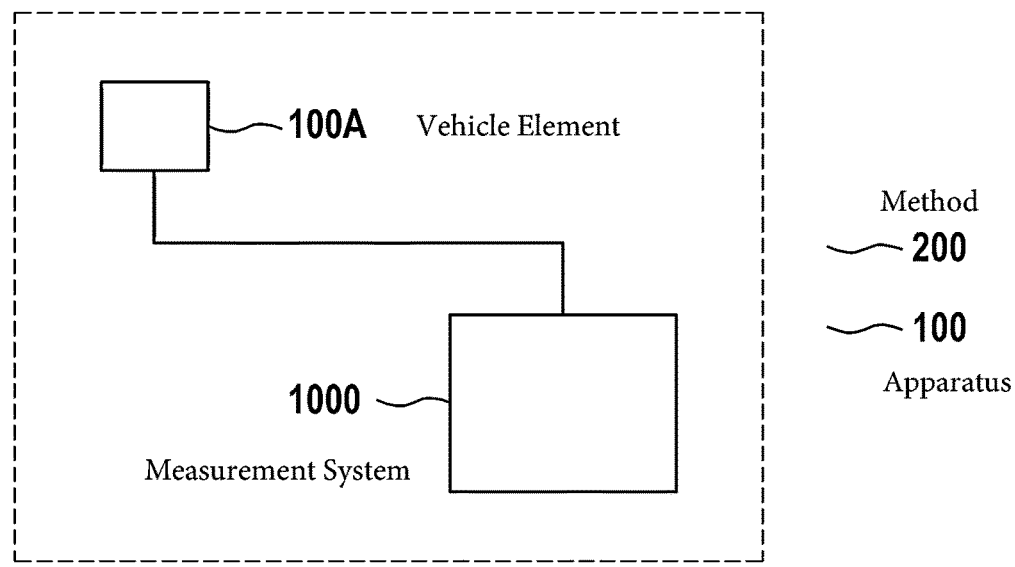
FIG. 1A shows a method for monitoring a driver of a vehicle by means of a measurement system.
Figure 1B:
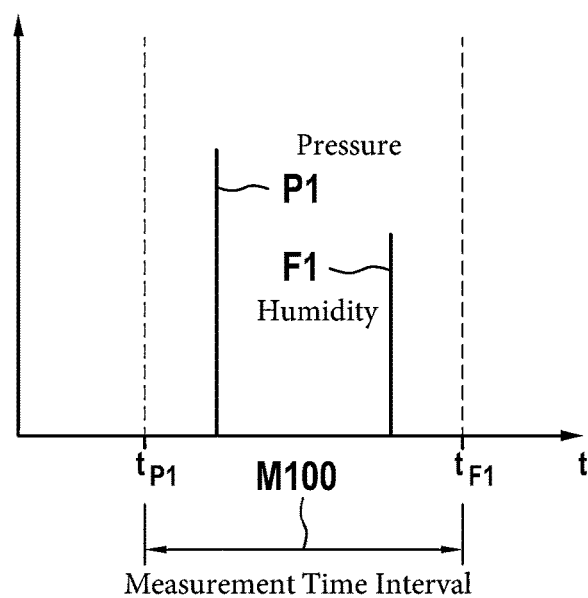
FIG. 1B shows measurement times within a measurement interval in a timing diagram.

FIG. 1B shows, in one possible embodiment, that a pressure P1 and a humidity F1 are in each case measured at different times within a predetermined measurement time interval M100. However, it is also possible to measure both values at the same time.

FIG. 2A shows a section of a schematic structure of a measurement system 1000 according to the invention described here. A processing unit 5, which is in data communication with a plurality of sensors 1, can be seen. The processing unit 5, together with the sensors 1, forms an apparatus 100. The humidity and/or pressure values measured by the individual sensors 1 are sent to a CPU 40 in order to be stored there and/or further processed. In addition, a temperature sensor 60 is shown which measures an ambient temperature and/or a temperature of the sensor 1 and forwards it to the processing unit 5 of the apparatus 100 and/or to the CPU 40.

Figure 2B:
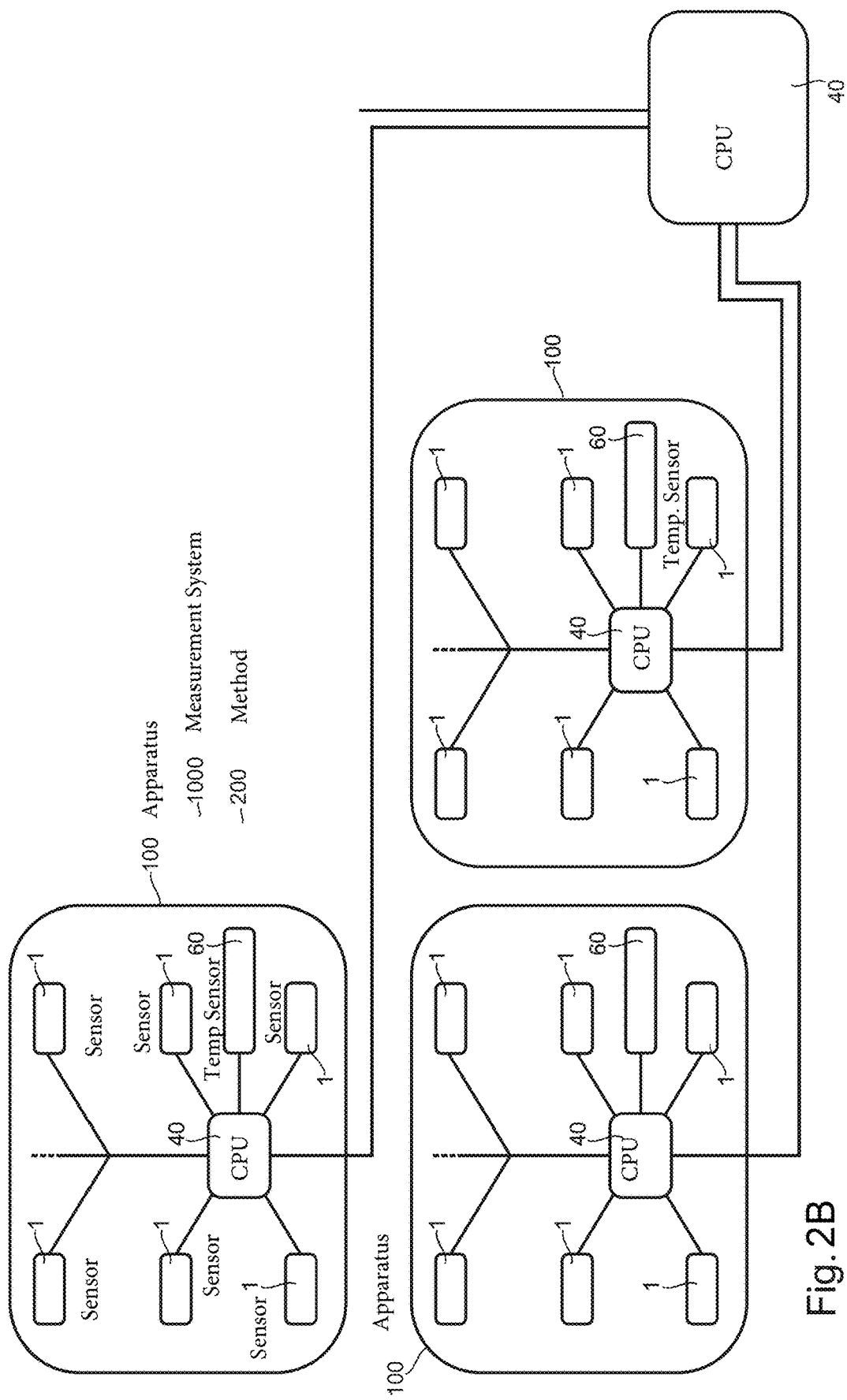

FIG. 2B schematically shows the entire measurement system 1000 with a plurality of sensor groups which are formed by the individual apparatuses 100 for measuring pressure and/or humidity and which each show a processing unit 5. Each processing unit 5 is therefore associated with a plurality of sensors 1.

Figure 2C:
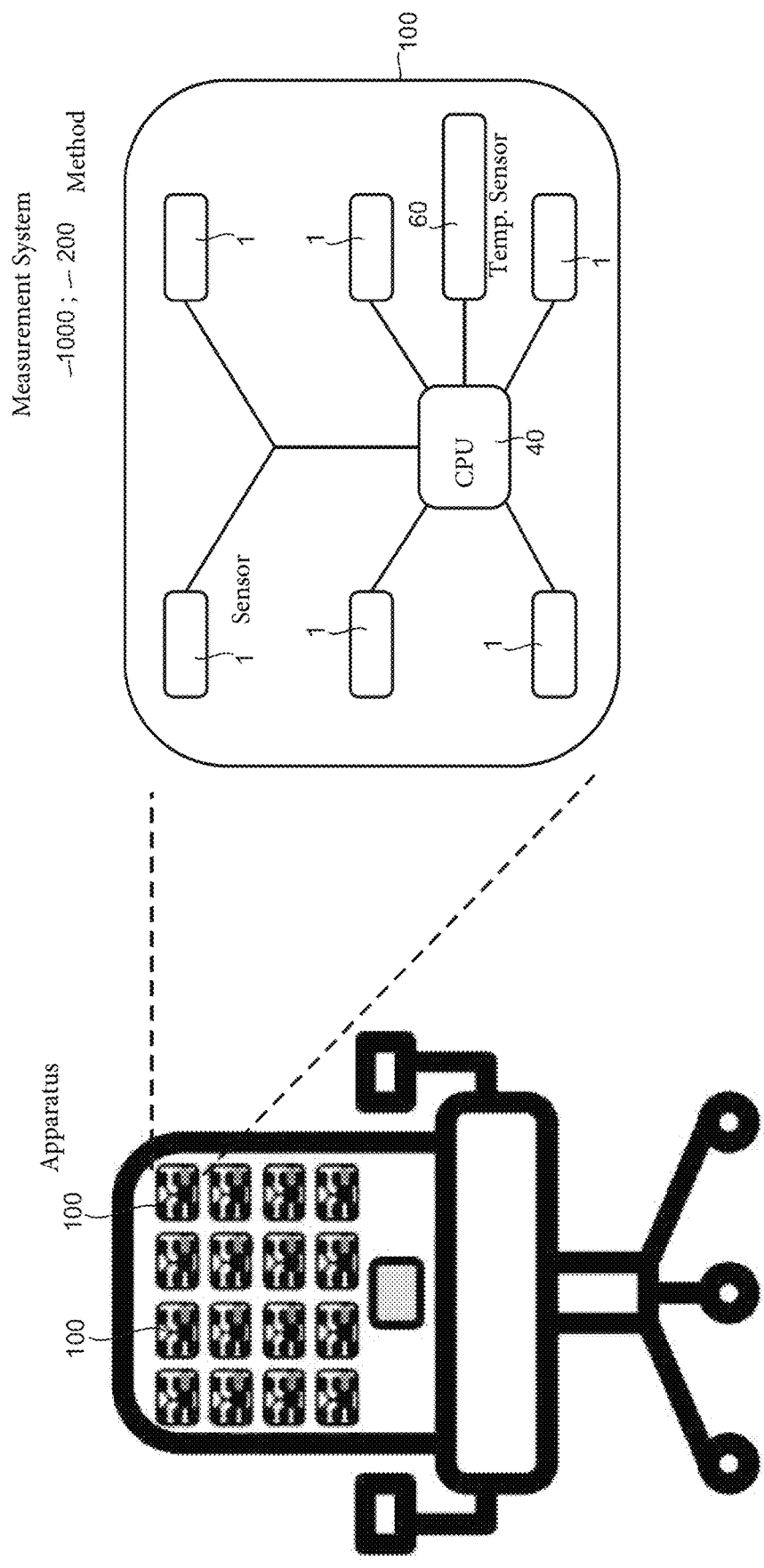

FIG. 2C schematically shows an installation and integration of the measurement system 1000 into a chair, in particular into an office chair.

Figure 3:
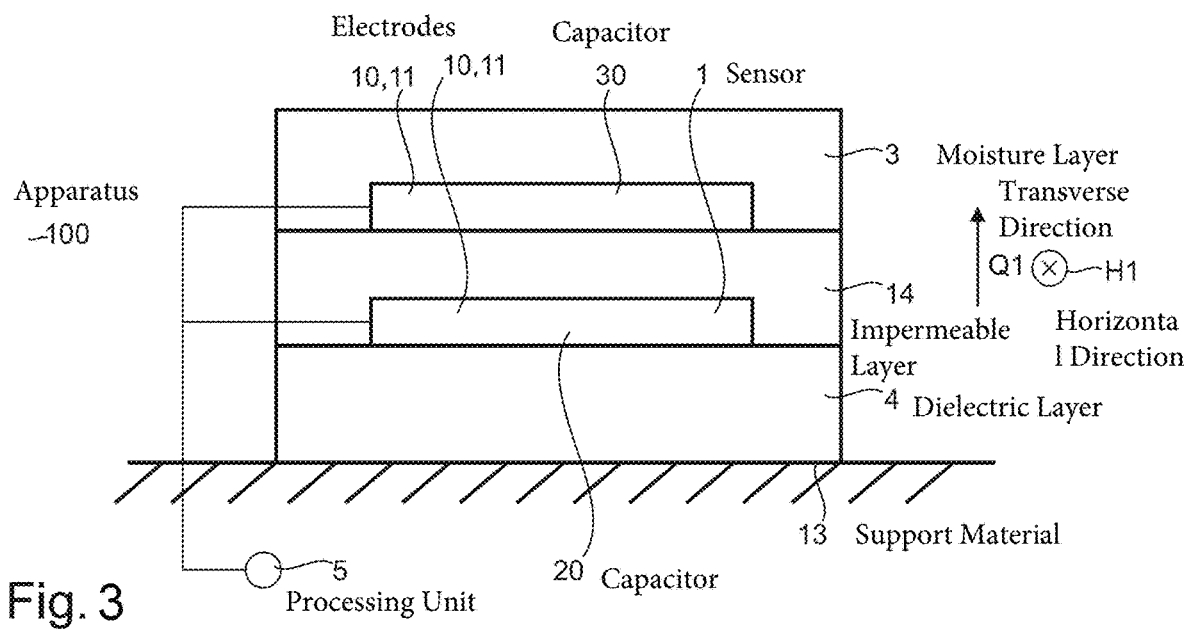
FIG. 3 shows an apparatus according to the invention for measuring pressure and/or humidity in a first embodiment.

As can now be seen in FIG. 3, an apparatus 100 for measuring pressure and/or humidity is shown in detail there.

By way of example, a sensor 1 is shown there, wherein the sensor 1 shows a capacitor stack having a capacitor 20 as well as a capacitor 30, wherein the individual electrodes 10, 11 of the capacitors 20, 30 are arranged one above the other in the horizontal direction H1, wherein an arrangement of the individual electrodes 10, 11 of a single capacitor 20, 30 can of course alternatively, however, extend or be arranged in the transverse direction Q1 which is perpendicular to the horizontal direction H1 and thus also perpendicular to the main extension direction of the sensor 1 shown there.

The individual electrodes 10, 11 are arranged on a support material 13. The support material 13 can in particular be a woven fabric, in particular a flexible woven fabric.

A water-impermeable layer 4 is arranged on the support material 13, wherein the two electrodes 10, 11 of the capacitor 20 are printed on this water-impermeable layer 4 in the horizontal direction H1.

The electrodes 10, 11 of the capacitor 20 are completely surrounded by another water-impermeable layer 14. The further capacitor 30 is printed in the same manner on this water-impermeable layer 14 with corresponding electrodes 10, 11. In the present embodiment, exposed outer surfaces of the individual electrodes 10, 11 of the further capacitor 30 are also preferably completely surrounded by a water-permeable and/or water-absorbing moisture layer 3.

Water can impinge on a dielectric layer 4 via this moisture layer 3, which dielectric layer is, in the present case, arranged in the horizontal direction H1 between the respective electrodes 10, 11 of a capacitor 20, 30.

Figure 4:
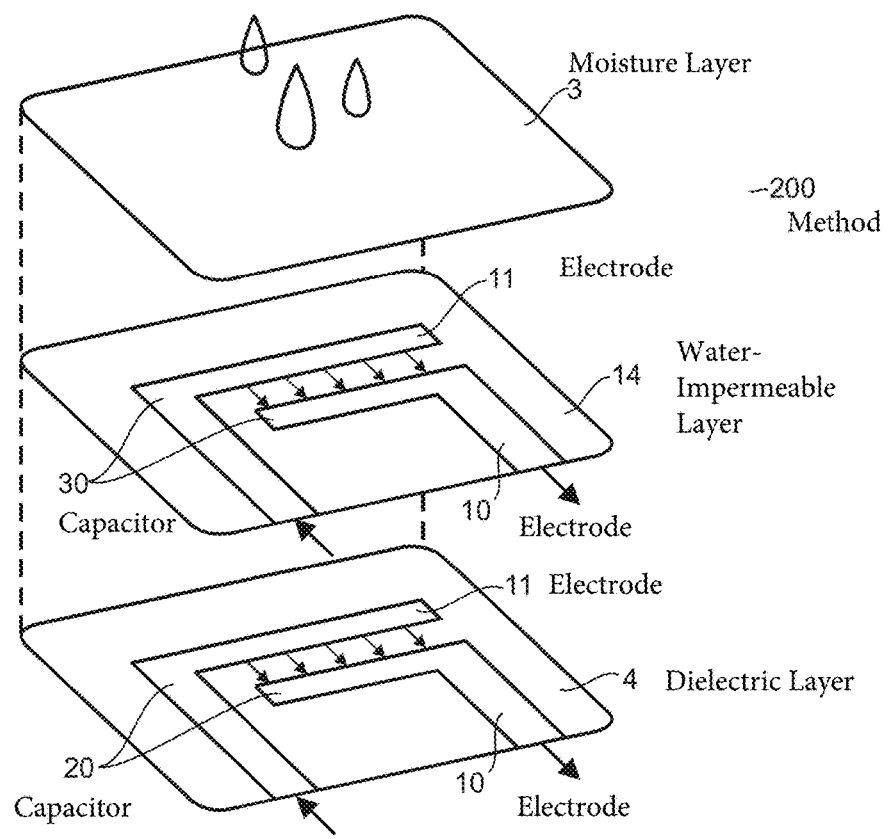
FIG. 4 is an exploded view of the layer arrangement in a schematic perspective view.
Figure 5:
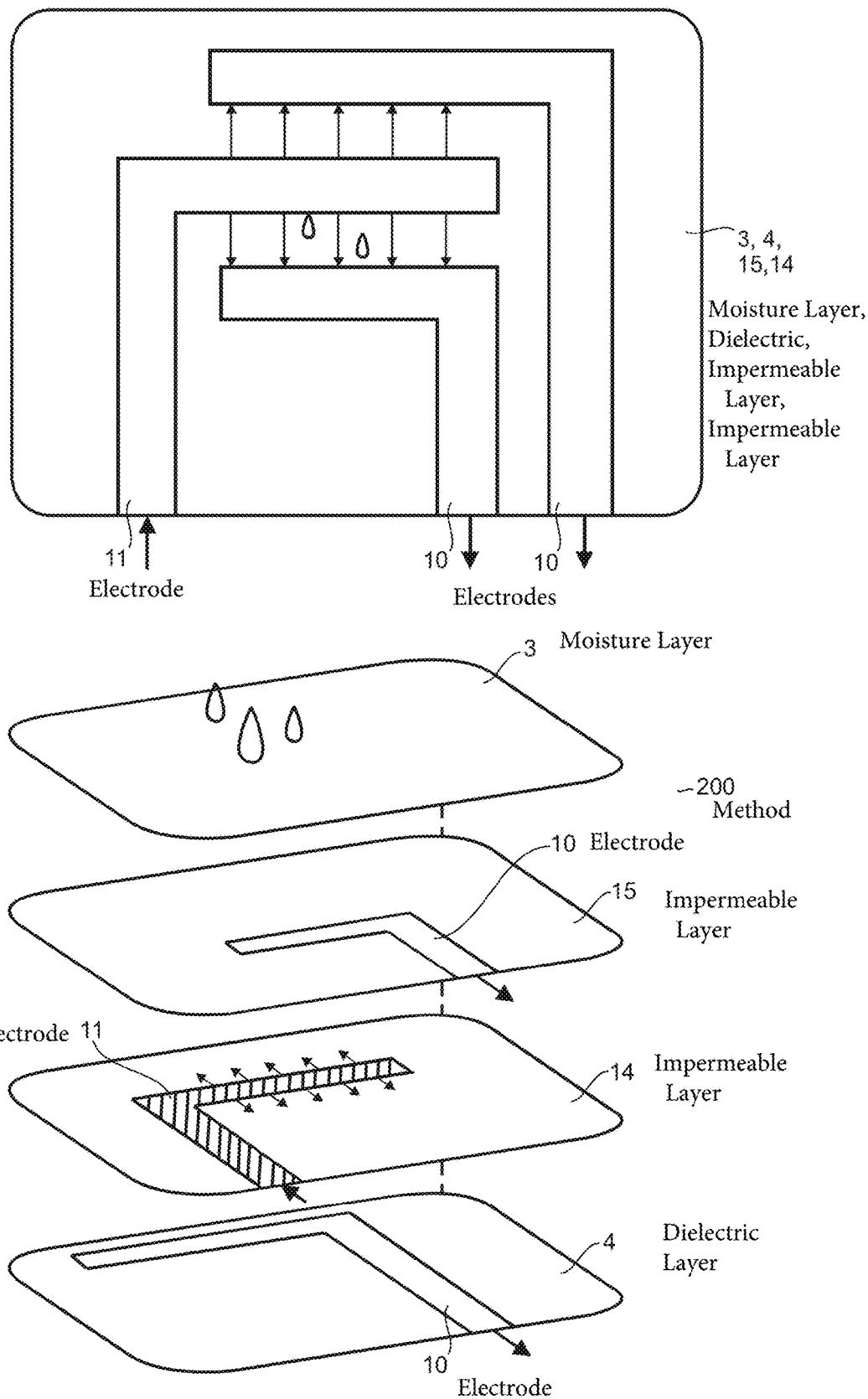
FIG. 5 shows a further embodiment of an apparatus described here.

In the present embodiment of FIGS. 3 and 4, the water-impermeable layer 4 itself forms a dielectric layer 4 of the capacitor 20. The same applies to the further water-impermeable layer 14 with respect to the further capacitor 30.

Due to the impingement and penetration of moisture via the moisture layer 3, the dielectric properties, in particular of the dielectric layer 4 of the further capacitor 30, are changed.

In addition, a processing unit 5 can be seen which is connected to the two capacitors 20, 30 by way of data technology, wherein this processing unit 5 is configured and provided to measure a change in the relative humidity of the environment and/or in the moisture layer 3.

The 'stackwise' arrangement shown in FIG. 4 and the fact that the further water-impermeable layer 14 prevents the capacitor 20 from coming into contact with moisture therefore make it possible to provide that only the further capacitor 30 and its dielectric layer 4 are exposed to moisture. For this purpose, the processing unit 5 can then compare a change in the capacitance of the further capacitor 30 with the stable capacitor capacitance of the capacitor 20 such that a particularly simple comparison of the change in the relative humidity and/or the respective loading pressure can be produced.

The arrow shown in FIG. 3 also shows the direction in which pressure is applied to the sensor 1. Both can preferably be measured, evaluated and stored by the sensor 1 and in particular by the apparatus 100. This purpose is served in particular by the processing unit 5 shown as being essential in the invention, which can additionally measure and evaluate corresponding pressure values and thus related changes in the capacitance of the individual sensors 1 such that the processing unit 5 is additionally configured and provided for measuring and/or storing a capacitance change of the capacitor 20 and in particular of the other capacitor 30 caused by external pressure.

The moisture layer 3 can be flexible or non-flexible. In addition, it is possible for the moisture layer 3 to be formed as a woven fabric. In particular, it can be a woven fabric which has been mentioned by way of example in the introductory part of the present application. In addition, however, it is also possible for the moisture layer 3 to be a substrate which was applied, for example glued, onto the further capacitor 30, for example in the form of an epitaxial or adhesive process.

The water-impermeable layer 14 and/or the water-impermeable layer 15 can also be designed to be flexible and non-flexible, in particular also designed in the form of a woven fabric or a substrate in the same way as the moisture layer 3.

In addition, it is advantageously conceivable for the electrodes 10, 11 of the two capacitors 20, 30 to have been printed on the water-impermeable layer 14 and on the further water-impermeable layer 15 in the form of a printing process, for example in the form of an inkjet printing process.

FIG. 3 is an exploded view, wherein the respective arrangement of the electrodes 10, 11 of the capacitors 20, 30 is shown in particular in FIG. 3. The force acting on the sensor 1 shown by the direction of the arrow, as well as moisture acting by way of the individual, schematically shown droplets can again be seen. In particular, it can again be seen that the moisture in particular penetrates between the electrodes 10, 11 and has, for example, a considerable effect on the electrical property of the respective water-permeable layer 14 such that the capacitance of at least the further capacitor 30 changes in each case as illustrated in FIG. 1.

FIG. 4 shows, in a further embodiment of the invention described here, that the sensor 1 can consist of two electrodes 10, as well as one electrode 11. The electrodes 10 have a polarity (preferably the same polarity), whereas the electrode 11 has a different polarity, wherein the lower part of FIG. 3, however, shows the exploded view of the left part of FIG. 3 and it can be seen that three water-impermeable layers 4, 14, 15 are used. The electrodes 10 can also have different polarities and/or electrical potentials. The electrodes 10 can also be electrically connected to each other.

For example, the electrodes 10, 11 can each also have and/or generate a separate polarity and/or a separate electrical potential. The same can also apply to the following drawings with respect to the electrodes.

For example, the lowermost water-impermeable layer is in turn the water-impermeable layer 4 and the subsequent water-impermeable layer 14 and the water-impermeable layer 15 arranged thereon in the transverse direction Q1 are another water-impermeable layer, wherein in each case one electrode 10, 11 is applied, in particular printed on a separate water-impermeable layer in each case.

In this stacking of the individual water-impermeable layers 4, 14 and 15, the capacitor 20 shown in the left part of FIG. 4 is therefore produced by merging these layers, wherein the electrodes 10 can, in each case, be arranged on different planes in the transverse direction Q1, as can be seen in the corresponding partial illustration.

Alternatively, the electrode 11 can be applied in a common plane, i.e. on or in a common water-impermeable layer 4, 14, 15, together with at least one of the electrodes 10 such that, for example, only the second of the electrodes 10 must be stacked on a separate water-impermeable layer 4, 14, 15.

In principle, therefore, the individual electrodes 10, 11 can be arranged in different planes relative to one another in the Q1 direction. For example, a paired association between exactly one water-impermeable layer 4, 14, 15 and exactly one electrode 10, 11 applies.

The invention is not limited by the description with reference to the embodiment. On the contrary, the invention encompasses each novel feature, as well as any combination of features, in particular including any combination of features in the claims, even if this feature or this combination itself is not explicitly mentioned in the claims or in the embodiments.

LIST OF REFERENCE SIGNS 1 sensor
3 moisture layer
4 dielectric layer/water-impermeable layer
5 processing unit
10 electrode
11 electrode
13 support material
14 water-impermeable layer
15 water-impermeable layer
20 capacitor
30 capacitor
40 CPU
60 temperature sensor
100 apparatus
100A vehicle element
200 method
1000 measurement system
P1 pressure
F1 humidity
H1 horizontal direction
M100 measurement time interval
Q1 transverse direction

The invention claimed is:

1. A method for monitoring a driver of a vehicle by means of a measurement system, wherein the method comprises the following steps:
a) providing a sensor, wherein,
at least one capacitors has at least two electrodes which are arranged in a horizontal direction along and on a flexible carrier material with respect to one another, at least one dielectric layers being arranged between the at least two electrodes, and the sensor has at least one further capacitors which is arranged in a transverse direction above or below the at least one capacitors and is arranged spaced apart from the at least one capacitors by a water-impermeable layer, so that a capacitor stack is formed, and both the at least one capacitors and the at least one further capacitors are constructed in the same way, and further wherein the at least one capacitors and the at least one further capacitors forming the capacitor stack perform the same tasks, and
further wherein the measuring system comprises at least two sensors, in communication with a Central Processing Unit (CPU) wherein the at least two sensors are divided into groups of at least one sensor, functionally by the CPU, based on at least the following criteria:
arrangement location of the at least two sensors on the carrier material, wherein the carrier material is divided into area regions, and within an area region only sensors of one group are arranged, wherein,
at least one of the capacitors is arranged on a side facing away from the carrier material having at least one electrodes and/or the at least one dielectric layers, at least one at least partially liquid-permeable and/or liquid-absorbing moisture layers is arranged at least in places on a side of the at least one electrodes facing away from the carrier material and/or the at least one dielectric layers,
the at least one electrodes and/or the at least one dielectric layers thus being arranged in a transverse direction between the carrier material and the at least one moisture layers so that a capacitance is at least partially changed by a liquid at least partially impinging on the dielectric layers, wherein
a processing unit is set up and provided for measuring and/or storing the capacitance change, so that a capacitive humidity sensor is produced, wherein the sensor is additionally a capacitive pressure sensor, wherein
the processing unit is additionally adapted and provided for measuring and/or storing a capacitance change of the capacitive pressure sensor caused by external pressure, and
further wherein the capacitive pressure sensor is one in which the capacitance change due to the deflection of a membrane and the resulting change in a plate spacing is evaluated as a sensor effect, so that the membrane is the at least one dielectric layer or the at least one electrodes,
b) providing at least one measurement system for measuring pressure and/or humidity, wherein the measurement system is coupled to at least one vehicle element or is installed with at least one in an integrated manner and the measurement system has at least one of the sensors for measuring a stress level of the driver such that the sensor measures pressure and/or humidity;
c) subsequent forwarding of the pressure and/or humidity values, to the central processing unit (CPU) of the measurement system;
d) detecting and recognizing a stress level of the driver based on the pressure and/or humidity values; and
e) determining a selected action based on the pressure and/or humidity values as measured by the measurement system, wherein the action is selected from the actions consisting of: setting up a call to a remote support center, transmitting the stress level value to a remote support center, generating an audible alarm and generating a visual alarm, adjusting a volume of speakers in the vehicle, adjusting a seat position of a vehicle seat of the vehicle, and displaying break recommendations to the driver.

2. The method according to claim 1 characterized in that the sensor measures only the pressure or the humidity to determine the stress level of the driver.

3. The method according to claim 1, characterized in that the sensor is installed in a steering wheel and/or a joystick and/or a vehicle seat of the vehicle such that the driver directly touches the steering wheel and/or the joystick and/or the vehicle seat.

4. The method according to claim 1, characterized in that a memory of the Central Processing Unit (CPU) stores limit values of pressure and/or humidity, wherein the pressure and humidity values measured in a time-discrete or continuous manner in each case are compared to the limit values stored in the memory of the CPU, wherein the CPU determines an action to execute if at least one of the humidity and pressure values is exceeded.

5. The method according to claim 4, characterized in that the memory of the CPU stores factor limit values of pressure and/or humidity, wherein the pressure and humidity values measured in a time-discrete and continuous manner in each case are compared to the factor limit values stored in the memory of the CPU, wherein the CPU determines an action to execute if at least one of the humidity and pressure values is exceeded, wherein the factor limit value is defined as a factor of the respective pressure and humidity value, in particular wherein the sensor measures both pressure and humidity values at the same time.

6. The method according to claim 1, characterized in that the pressure and the humidity values are in each case measured at different times within a predetermined measurement time interval.

7. The method according to claim 6, characterized in that within the predetermined measurement time interval, the pressure and/or a temperature is/are measured first and the humidity and/or the temperature is/are only measured afterwards, wherein the pressure and the humidity are measured only once within each measurement time interval.

8. The method according to claim 6, characterized in that a time interval between two measurement intervals immediately adjacent to each other in terms of time is greater than the period of at least one of the measurement intervals, in particular wherein no measurement takes place in measurement breaks generated thereby.

9. An apparatus for monitoring a driver of a vehicle by means of a measurement system for carrying out the method according to claim 1.

10. The apparatus according to claim 9, characterized by the measurement system for measuring pressure and/or humidity, wherein the measurement system is coupled to at least one vehicle element or is installed or installable with at least one in an integrated manner, wherein the measurement system has at least one sensor for measuring a pressure and/or humidity values and subsequently calculates and transmits a driver stress level from such values.

\* \* \* \* \*